(12) United States Patent
Dekker et al.

(10) Patent No.: US 7,763,706 B1
(45) Date of Patent: Jul. 27, 2010

(54) ARGININE/LYSINE-ENRICHED PEPTIDES

(75) Inventors: Anita Dekker, Wageningen (NL);
Johanna Maria Henrica van der Steen, Berlicum (NL)

(73) Assignee: Campina B.V., Zaltbommel (NL)

( * ) Notice: Subject to any disclaimer, the term of this patent is extended or adjusted under 35 U.S.C. 154(b) by 679 days.

(21) Appl. No.: 10/564,796

(22) PCT Filed: Jul. 11, 2003

(86) PCT No.: PCT/NL03/00526

§ 371 (c)(1),
(2), (4) Date: Feb. 28, 2007

(87) PCT Pub. No.: WO2005/007680

PCT Pub. Date: Jan. 27, 2005

(51) Int. Cl.
*B01D 15/01* (2006.01)
*A61K 38/00* (2006.01)

(52) U.S. Cl. ............... 530/305; 530/228; 530/300; 424/124

(58) Field of Classification Search ............ None
See application file for complete search history.

(56) References Cited

U.S. PATENT DOCUMENTS

| 5,317,084 | A * | 5/1994 | Tomita et al. ............ 530/324 |
| 6,288,212 | B1  | 9/2001 | Hancock et al. |
| 2005/0196443 | A1 * | 9/2005 | Weinbach et al. ......... 424/469 |
| 2007/0104764 | A1 * | 5/2007 | Jensen et al. ............ 424/442 |
| 2008/0207487 | A1 * | 8/2008 | DeFrees et al. ............ 514/2 |

FOREIGN PATENT DOCUMENTS

| EP | 0 799 577 A | 10/1997 |
| JP | 02 182169 A | 7/1990 |
| WO | WO 99 31123 A | 6/1999 |

OTHER PUBLICATIONS

Orff et al. (2009) Extracorporeal circulation can induce hypotension by both blood-material contact and pump-induced platelet aggregation, J. Thorac. Cardiovasc. Surg., vol. 120, pp. 12-19.*
Wikipedia (2009, updated) "Ionic strength", http://en.wikipedia.org/wiki/Ionic_strength, pp. 1 and 2.*
Josefina et al. (2005) "Amino acid composition of some Mexican foods", pp. 1-12.*
Susheelamma NS: "Studies on Lysine Enriched plasteins from Oilseed Proteins" Journal of Food Science and Technology, India, vol. 20, No. 2, 1983, pp. 47-51 XP008026612 the whole documenht.
Bargeman G. et al.: "Selective isolation of cationic amino acids and peptides by electro-membrane filtration" LAIT, vol. 80, 2000, pp. 175-185, XP008026611 the whole document.
Patent Abstracts of Japan vol. 014, No. 456 (C-0765), Oct. 2, 1990. (Not Attached).

* cited by examiner

*Primary Examiner*—Manjunath N Rao
*Assistant Examiner*—Samuel Liu
(74) *Attorney, Agent, or Firm*—Greenberg Traurig, LLP

(57) ABSTRACT

Described is a method for the preparation of a mixture of peptides, having an arginine and lysine content of at least 20 w/w %, based on the protein content, from at least one protein source, to a preparation comprising a mixture of arginine- and lysine-rich peptides, comprising at least 20 w/w % arginine and lysine, and to the use of the said preparation as active compound in a medicament, supplement, beverage or food product.

10 Claims, No Drawings

ARGININE/LYSINE-ENRICHED PEPTIDES

This application is a national stage filing under 35 U.S.C. 371 of International Application PCT/NL03/00526, filed on Jul. 11, 2003. International Application PCT/NL03/00526 was published under No. WO 2005/007680 on Jan. 27, 2005.

The invention relates to a method for the preparation of a mixture of peptides, having an arginine and lysine content of at least 20 w/w %, based on total protein content, from at least one protein source, to preparations comprising said mixture of peptides and to the use of such preparations as active compound in a medicament, supplement, beverage or food product.

Peptides are herein defined as amino acid chains, derived from a protein; the molecular weight of the peptides is below 10,000 Da, more preferably below 5,000 Da, most preferably below 2,000 Da.

The importance of a healthy diet is widely acknowledged. Amino acids, peptides and proteins are important constituents of food. They do not only supply the required building blocks for protein synthesis, they also play important roles in several metabolic pathways in the mammalian body.

Biochemically, arginine appears to be an essential amino acid under certain metabolic conditions. Arginine is involved in several processes in the body, from wound healing to helping to maintain the immune system. It is also a precursor to nitric oxide (NO), which helps the body keep blood vessels dilated, allowing the heart to receive an adequate supply of oxygen. Lysine is a limiting factor in the biological value of many proteins, as processing of food products often results in losses of lysine since its ε-amino group is highly reactive towards other food ingredients. Lysine is involved in tissue repair, growth, and the production of enzymes, hormones, and antibodies. It is also vital for collagen synthesis and bone health.

The implication of arginine for improving vascular function has been described (see e.g. US Patent Application 0 013 288, Napoli (2002) J. Card. Surg., 17(4):355-362). Blood vessels are lined with the endothelium. Impairments in the structure of the blood vessel walls (e.g. in arteriosclerosis) and tiny lesions in the endothelium result in adherence of monocytes, which penetrate the endothelial lining of blood vessels and end up in the subintimal space between the endothelium and the vascular smooth muscle of the blood vessels. These monocytes absorb increasing amounts of cholesterol (mainly oxidised or modified low-density lipoprotein (LDL)) to form foam cells. Oxidised LDL alters the endothelium, and the underlying foam cells distort the endothelium and may eventually even rupture through it.

Endothelial disruption leads to adherence of platelets at this site and to release of a number of growth factors. One of these growth factors, platelet derived growth factor (PDGF), stimulates migration and proliferation of vascular smooth muscle cell into the lesion. These smooth muscle cells release extracellular matrix (collagen and elastin) and the lesion continues to expand. Macrophages in the lesion release proteases, and the cell is damaged as a result of this. As a consequence, a necrotic core is created that is filled with cellular debris and lipid. This is also referred to as a "complex lesion". Rupture of such a lesion can lead to thrombosis and occlusion of the blood vessel. In a coronary artery, rupture of a complex lesion may precipitate a myocardial infarction, whereas in the case of carotid artery, a stroke may occur.

Arteriosclerosis, thrombosis and restenosis are all characterised by a loss of normal vascular function, such that vessels tend to constrict, rather than dilate. This abnormal vascular function (referred to hereinafter as "excessive vasoconstriction") occurs in other disease states such as angina (in case of a heart artery), transient cerebral ischemia (in case of a brain vessel), hypertension, congestive heart failure, toxaemia of pregnancy, Raynaud's phenomenon, Prinzmetal's angina (coronary vasospasm), cerebral vasospasm, haemolytic uraemia and impotence. These disorders are related to abnormality of vascular function and structure and have a high prevalence as well as serious consequences. Hence, it is highly important to find therapies that will diminish excessive vasoconstriction.

The pathological processes described above are extremely complex. A substance released by the endothelium, "endothelium derived relaxing factor" (EDRF), may play an important role by the inhibition of these pathological processes. This EDRF has been shown to be nitric oxide (NO) or a labile nitroso compound that liberates NO (hereinafter also referred to as "NO"). EDRF (i.e. NO) relaxes vascular smooth muscle, inhibits platelet aggregation, mitogenesis, proliferation of cultured vascular smooth muscle, and leukocyte adherence. Therefore, NO is the most potent endogenous vasodilator and increased NO bioavailability could prevent and/or treat the above disorders. Moreover, NO is largely responsible for exercise-induced vasodilation in the conduit arteries. Therefore, enhancement of NO synthesis (and/or bioavailability) could also improve exercise capacity in normal individuals and those with vascular disease.

Both arginine and lysine are precursors in the metabolic pathway to the production of nitric oxide. They act as substrate for nitric oxide synthetase (NOS), the enzyme responsible for the production of nitric oxide. It has been described that synthesis of EDRF (i.e. NO) can be increased by arginine in subjects diagnosed with hypercholesterolemia. This is effectuated by release of NO from the vessel wall. Moreover, administration of arginine has been shown to inhibit monocytes from sticking to the blood vessel, as well as platelet aggregation.

A diabetic environment high in free radicals and low in antioxidants may likewise disrupt endothelial function. Diabetes heightens the tendency for blood clotting, and increases risk for stroke and myocardial infarction. Administration of arginine restores diabetic NO levels toward normal values (Witte, M. B. et al. (2002) Metabolism 51:1269-1273). Hence arginine supplementation can be used to decrease the detrimental effect diabetes exerts on endothelial function.

Not only does the dilating effect of nitric oxide generated through administration of lysine and/or arginine play a role in improvement and/or restoration of vascular function, it also results in an increase in aerobic capacity in said subjects (see e.g. Maxwell et al. (2001) J. Appl. Physiol. 90:933-938). Enhanced endogenous NO production caused by the addition of precursors of NO such as arginine and lysine can increase the blood flow by reducing the number of blood elements adhering to the lumen of the vessel. An increased blood flow can advantageously lead to increased aerobic capacity and increased removal of lactic acid, which is formed in the muscles upon exercising.

In addition to this function, arginine stimulates the secretion of growth hormone from the pituitary gland (see e.g. Chromiak et Antonio (2002) Nutrition 18:657-661). Many studies show an elevation in growth hormone levels upon administration of arginine, particularly in combination with lysine. Further, arginine stimulates pancreatic release of glucagon and insulin, and thereby aids in the regulation of blood glucose levels in subjects with diabetes.

Moreover, arginine, particularly in combination with lysine, enhances immune function by stimulating the thymus gland to produce additional T cells (see e.g. Potenza et al. (2001) Curr. Drug Targets Immune Endocr. Metabol. Disord. 1:67-77).

Therefore, in the art there is a demand for compounds comprising the positively charged amino acids arginine and lysine for effective administration of said amino acids to the human or animal body.

U.S. Pat. No. 5,902,829 discloses the use of arginine as a free amino acid in the preparation of a medicament or nutritional formulation for the improvement of micro-circulatory hypoperfusion and/or treatment or prophylaxis of hypoperfusion-reperfusion injury for preoperative administration.

US Patent Application 20020013288 discloses a method of improving function and structure of the vascular system by administration of arginine and lysine as free amino acids to enhance endogenous NO levels in the vascular system to improve vascular function.

However, for effectuating the above beneficial effects to a subject, relatively large amounts of arginine and lysine have to be administered. The administration of large amounts of free amino acids is associated with several problems. Unfortunately, the free amino acids arginine and lysine have an undesirable flavour, are highly basic and can readily react with a variety of other chemicals, which may be consumed simultaneously with the amino acids. Moreover, free arginine, administered in high doses, may cause intestinal problems, like diarrhea. Another disadvantage of the use of free arginine and/or lysine is the high osmolarity obtained by dissolution of mixtures thereof, which is considered a disadvantage in certain applications in the field of medical nutrition.

The above-identified problems may be avoided by providing an amino acid composition rich in arginine and/or lysine in the form of a peptide rather than in the form of free amino acids. This provides another advantage over the use of free amino acids, i.e. the fact that uptake of amino acids in the gut takes place more efficiently when they are provided in the form of a peptide, in comparison with the free amino acids.

Peptides can be obtained either by chemical synthesis or by cleavage of natural protein sources. As synthetic peptides are tediously and costly to produce, the industrially preferred method for obtaining peptides is the cleavage of natural protein sources. However, the yield in arginine and/or lysine is limited to the natural content of arginine/lysine of the starting material, i.e. at least one protein source. By solely cleaving natural protein sources, the total yield in arginine and lysine is limited to about 10 w/w %, based on total protein content.

The present invention solves the above problem by providing large amounts of the amino acids arginine and lysine in the form of a mixture of peptides which are derived from at least one protein source, preferably a natural protein source. According to the present invention, a novel method is provided for the preparation of a mixture of peptides, having an arginine and lysine content of at least 20 w/w %, preferably at least 30 w/w %, more preferably at least 40 w/w %, based on total protein content, from at least one protein source.

The method is characterised in that it comprises the steps of:

a) cleaving the proteins of at least one protein source into peptides;

b) allowing the peptides to bind to cation exchange resin;

c) washing the cation exchange resin with an alkaline wash solution having a normality of 0.05-2.0;

d) eluting bound peptides from the resin with an aqueous elution solution having an ionic strength of at most 200 mM and a pH between 5.0-9.0.

While the flavour of the free amino acids is often undesirable, said peptides are generally neutral in taste, and can be provided in large amounts at low cost.

The term "arginine and lysine content" means that the given content reflects to the combined arginine and lysine content. A peptide mixture having an arginine and lysine content of e.g. 20 w/w % means that from the total protein content, 20 w/w % thereof is constituted by arginine and lysine. It is possible that the arginine content is 20 w/w % and that no lysine is present, or vice versa. However, any combination amounting to a total of 20 w/w % is possible, such as e.g. 13 w/w % arginine and 7 w/w % lysine. The peptide mixture according to the invention preferably comprises at least 10 w/w % arginine and 10 w/w % lysine, more preferably at least 15 w/w % arginine and 15 w/w % lysine, most preferably at least 20 w/w % arginine and 20 w/w % lysine.

In the first step a) proteins from at least one protein source are cleaved into smaller peptides. This cleavage can be performed by cleavage reactions well known in the art, such as enzymatic and chemical cleavage reactions.

In step b) the peptide mixture solution is passed through a cation exchange resin. Cation exchange resins are generally made up of matrices of porous, (cross-linked) copolymers of styrene/divinylbenzene or cellulose, that expose either a weakly acidic ligand (carboxylic acid) or a strongly acidic ligand (sulfonic acid). Any cation exchange resin can be used for the method of the invention. Non-limiting examples of such resins are Amberlite IRC 50, resin IMAC HP 1110Na, from Rohm & Haas Inc., USA, (Rohm & Haas, USA), Lewatit S2328, Lewatit S2528 (Sybron Chemicals Inc., Germany), Gibco SP IEC HB4 (Life Technologies, New Zealand) and Toyopearl SP-550C (Tosoh Biosep, Germany). The cation exchange resin is generally preconditioned according to the instructions of the manufacturer. It is preferred that the resin is present in a column, as this facilitates purification steps. Preferably, the peptides are loaded onto said resin in an aqueous solution, preferably having a pH of 5.0-9.0, more preferably a pH of 6.0-8.0. Under such conditions, sufficiently positively charged peptides, such as arginine- and lysine-rich peptides, preferentially bind to the negatively charged resin, whereas neutral and acidic peptides will pass through the resin without substantially interacting therewith. As a result, arginine- and lysine-rich peptides according to the present invention will selectively bind to the resin.

In step c) the resin is subjected to a wash step with an alkaline solution having a normality of 0.05-2.0, preferably of 0.2-1.0, more preferably of 0.4-0.6. "Normality" is herein defined as the number of equivalents of solute per liter of solution and is mostly used to express the concentrations of acidic or alkaline solutions. One equivalent of a base is the amount of base that will react with one mole of hydrogen ions, e.g. a 1.0 M NaOH solution constitutes a 1.0 N NaOH solution, whereas a 1.0 M $CaOH_2$ constitutes a 2.0 N $CaOH_2$ solution (as it provides 2.0 M hydroxide ions). Any alkaline can be used, however, preferably said alkaline wash solution comprises sodium hydroxide.

In step d) bound peptides are eluted from the resin with an aqueous elution solution having an ionic strength of at most 200 mM, more preferably of at most 150 mM, yet more preferably of at most 100 mM, again more preferably of at most 50 mM, most preferably of at most 25 mM, and a pH between 5.0-9.0, more preferably between 6.0-8.0. Said elution solution can e.g. be demineralised water or a 50 mM $Na_2HPO$ solution, with a pH between 5.0-9.0, more preferably between 6.0-8.0.

Surprisingly, with such low salt elution step, elution of the peptide fraction precedes elution of the remaining salt present on the resin. Therefore, the peptide and the remaining salt do not elute simultaneously. Said elution step is advantageous as it avoids the use of high ionic strength (i.e. salt concentrations), commonly practised in the art. Such high-salt elution often demands the economically costly step of ultra- and/or diafiltration after elution required to remove salt.

According to the invention, elution takes place using a solution with low ionic strength, preferably demineralised water, thus avoiding the presence of undesired concentrations of salt in the peptide preparation. The ionic strength can be defined by $I=0.5 \Sigma c_i z_i^2$, wherein I represents the ionic strength, $c_i$ represents the concentration (moles of solute per liter of solvent) of the ith ion, and $z_i$ represents the charge of the ith ion. E.g., a 50 mM $Na_2HPO_4$ solution corresponds with an ionic strength of $0.5\times([2\times50]\times1^2]+[50\times2^2]=150$ mM. A suitable ionic strength is generally achieved using salts such as sodium hydrogen phosphate, potassium hydrogen phosphate, sodium chloride, calcium chloride, potassium chloride, ammonium sulphate, and the like.

The peptide preparations according to the present invention will be ready for further processing (for example ultrafiltration to reduce the volume of the preparation, pH adjustment, drying and/or packaging) immediately after the elution step. Importantly, as elution is performed with a low ionic strength eluens, no costly steps of diafiltration are required to remove salt, used for elution of the peptides.

Further, the invention relates to a method as described above, comprising between steps b) and c) a prewash step, wherein said cation exchange resin is washed with a prewash solution having an ionic strength of at most 200 mM, more preferably of at most 150 mM, yet more preferably of at most 100 mM, again more preferably of at most 50 mM, most preferably of at most 25 mM, and a pH of between 5.0-9.0, preferably of between 6.0-8.0. Said prewash solution may be the same as used for elution of the peptides, or may be different. Thus, demineralised water may also be used for the prewash step. Surprisingly, it was found that positively charged peptides according to the present invention were retained on the cation exchange resin when said resin was washed with said prewash solution preceding the alkaline wash step, whereas the peptides were eluted when the cation exchange resin was washed with a similar or even identical solution after the alkaline wash step. Said prewash step is advantageous as it has been found that a more purified peptide preparation can be obtained.

In a preferred embodiment of the invention, the mixture of peptides that is obtained has an arginine and lysine content of at least 30 w/w %, preferably at least 40 w/w %, based on total protein content. More preferably, the arginine content is at least 15 w/w % and the lysine content is at least 15 w/w %, most preferably the arginine and lysine content are both at least 20 w/w %, based on total protein content. Such peptide mixtures are not available in nature and are highly suitable to overcome the above-mentioned problems.

Preferably, the cleavage of the proteins of at least one protein source (step a) comprises enzymatic hydrolysis of peptide bonds of the protein by e.g. one or more endopeptidase, resulting in peptides of a desired length. Non-limiting examples of commercially available endopeptidase preparations that can be used for enzymatic cleavage of at least one protein source are Alkalase, Chymotrypsine 800s, Neutrase (all available from Novo Nordisk, Denmark), Protex 6.0 L, Peptidase FP (both available from Genencor, USA), Corolase L10 (Rohm, Germany), Pepsin (Merck, Germany) and Protease N (Amano, Japan).

Optionally, step b) is preceded by a filtration step, preferably a microfiltration or ultrafiltration step. Preferably, said filtration step is carried out using a membrane having a cut-off of 10 kDa, but a filter with a different cut-off, such as 0.2 micron, may also be used. Said filtration step may be used to remove microbes or crude particles and can hence serve to purify the peptide solution preceding application thereof on the cation exchange resin, which is advantageous as it prevents contamination of the resin.

"At least one protein source" is herein defined as one or more protein sources. They may be any protein source as long as they comprise arginine- and/or lysine-containing proteins. The term "protein source" is to be understood to comprise any protein containing material from which proteins can be isolated. Preferably, the protein source is of natural origin, such as plant, animal or microbial material. Also, two protein sources may be combined wherein one protein source may e.g. be rich in arginine, whereas the other protein source may be rich in lysine. Examples of protein sources rich in arginine are soy, pea and cotton seed protein sources (about 8 w/w % arginine, based on total protein content), whereas crab proteins, fish proteins and whey proteins are rich in lysine (about 10-11 w/w % lysine, based on total protein content). Such protein sources are easily available at low cost and, importantly, they are food grade.

Preferably, the at least one protein source comprises at least two different proteins, that both contribute to the desired arginine and/or lysine content of the peptides. One of the proteins may be arginine-rich, whereas the second protein may be lysine-rich.

The at least one protein source preferably is of vegetable origin. Most preferably, the at least one protein source is chosen from the group, consisting of soy, pea and cotton seed. These protein sources are cheap, they are also accepted by vegetarians, and they intrinsically have both a high arginine and lysine content.

It is preferred that said at least one protein source comprises at least 10 w/w % arginine and lysine. Even more preferably, the at least one protein source comprises at least 5 w/w % arginine and at least 5 w/w % lysine, as starting with a high content of arginine and lysine gives better results, and it is preferred that both amino acids are present in a high concentration.

The invention further relates to preparations comprising a mixture of arginine- and lysine-rich peptides, comprising at least 20 w/w % arginine and lysine, more preferably at least 30 w/w % arginine and lysine, most preferably at least 40 w/w % arginine and lysine, based on total protein content. More preferably, said preparations comprise at least 10 w/w % arginine and at least 10 w/w % lysine, yet more preferably at least 15 w/w % arginine and at least 15 w/w % lysine, most preferably at least 20 w/w % arginine and at least 20 w/w % lysine, based on total protein content. Said preparations can advantageously be used for administration to subjects in order to improve vasodilation, to increase aerobic capacity, to stimulate the immune system, to stimulate growth hormone levels, to improve regulation of blood glucose levels in subjects with diabetes and to inhibit blood platelet aggregation. The invention also relates to the above-described peptide mixtures.

In addition, the invention relates to the use of a preparation according to the invention as active compound in a medicament, supplement, beverage or food product, in particular for elevation of nitric oxide blood levels.

For use in a medicament or supplement, said preparation can be combined with any suitable carrier, diluent, adjuvant, excipient, etc. in order to obtain the medicament in the desired administration form. Advantageously, said medicament or supplement is administered orally. The term "supplement" is meant to include food supplements, as well as health products, such as health drinks.

For the intended use, the arginine- and lysine-rich mixture of peptides according to the invention may be administered alone or in admixture with a pharmaceutically acceptable carrier, in suitable pharmaceutical formulations which are a further object of the invention.

Examples of said formulations, which may be prepared using well known methods and excipients, such as those described in "Remington's Pharmaceutical Sciences Handbook", Mack Pub. Co., N.Y. U.S.A., are tablets, capsules, syrups, and the like for oral administration, whereas for the parental administration suitable forms are sterile solutions or suspensions in acceptable liquids, implants, etc.

The posology will depend on several factors such as type and seriousness of the pathological conditions to be treated, patient's weight and sex, etc. and will be easily determined by the skilled practitioner.

For use in a beverage or food product, said preparation can be combined with any common food ingredient. The term "beverage" is meant to include cordials and syrups, as well as formulations of a dry powder to be dissolved in water or another beverage for the preparation of instant drinks.

In one embodiment, said preparation is used as active compound in a medicament, supplement, beverage or food product for increasing aerobic capacity and/or decreasing acidification in muscle tissue. Said preparation is advantageously used in a sports drink or sports food product. In such application, the preparation according to the invention is used to increase exercise capacity and to remove lactic acid from the muscle. Alternatively, it may be used to increase muscle building.

In another embodiment, said preparation is used as active compound in a medicament, supplement, beverage or food product for prophylaxis and/or treatment of disorders associated with reduced and/or inadequate vasodilation or increased blood platelet aggregation. In particular, said disorder is chosen from the group, consisting of arteriosclerosis, restenosis, thrombosis, hypertension, impotence, stroke and diabetes.

Moreover, the invention relates to a preparation according to the present invention as active compound in a medicament, supplement, beverage or food product for stimulating growth hormone levels, immune response or improved regulation of blood glucose levels.

The invention is now illustrated in the following examples, which are meant not to limit the scope of the invention in any way.

EXAMPLE 1

Preparation of Arginine/Lysine-Enriched Peptides from Soy Protein

A 12 w/w % Procon 2000 (Procon 2000 having a protein content of 75 w/w %)(Central Soya Company, USA) solution was prepared. 5% alkalase was added and the soy protein was hydrolysed for 6 hrs at 60° C. After hydrolysis, the pH was adjusted to 6.8 and the enzyme was inactivated by passing the solution through a HTST pasteuriser (approx. 3 min at 110° C.). Subsequently, the solution was passed through a Hyflo diatomaeious earth filter.

The hydrolysate solution was loaded onto cation exchange resin Lewatit S2328 (flow rate=5 bed volumes/hr)(A bed volume is herein defined as the volume that corresponds with the volume of the resin in the column). Subsequently, the column was first washed with 2 bed volumes demineralised water, followed by a second wash with 1 bed volume 0.25 M NaOH (the flow rate during the wash step is 5 bed volumes/ hr). Next, the arginine- and lysine-rich peptides were eluted with 1.5 bed volumes demineralised water.

The content of arginine was determined according to Smith and MacQuarrie ((1978) Anal. Biochem. 90: 246-255). The content of lysine was determined using an amino acid analysis (with the acid hydrolysis method), as described in the directive 98/64/EEC, dated Sep. 3, 1998, that was published in the Official Journal European Community (1998, L257/14-28, dated Sep. 19, 1998). The total amount of protein was determined using Kjeldahl according to the method of the International Dairy Federation IDF-FIL 20A (1986).

The eluate contained the arginine- and lysine-enriched peptides with a purity level of 15 w/w % arginine and 15 w/w % lysine, based on total protein content. The eluate fraction was adjusted to pH 7.0, and freeze-dried to obtain a powder product. The powder had a protein content of 95 w/w %, based on total product. The protein:salt ratio (w/w) was 20:1.

The molecular weight distribution of peptide preparations was determined chromatographically using a Superdex Peptide R 10/30 column (Pharmacia, Sweden) by determining the optical density at 214 nm. The column was eluted with 0.02 M $Na_2HPO_4$ and 0.25 M NaCl, pH 7.2 (using a flow rate of 0.4 ml/min.). Table 1 shows the molecular weight distribution of the peptide preparation.

TABLE 1

Molecular weight distribution of the peptide preparation.

| Molecular weight | % of peptides |
|---|---|
| <0.1 kD | 13 |
| 0.1-0.5 kD | 55 |
| 0.5-1 kD | 20 |
| 1-2 kD | 10 |
| 2-5 kD | <10 |
| 5-10 kD | <1 |
| >10 kD | <0.5 |

COMPARATIVE EXAMPLE 1A

Soy protein was hydrolysed as described in Example 1. The hydrolysate solution was loaded onto cation exchange resin Lewatit S2328 (flow rate=5 bed volumes/hr). Subsequently, the peptides were eluted with 1 M NaCl.

The content of arginine, lysine and protein was determined as described in Example 1. The obtained peptide fraction yielded arginine and lysine contents that were comparable to those achieved in Example 1; However, the protein:salt ratio (w/w) was 1:9. The product had a 180 times higher salt content in comparison with the product of Example 1 and therefore extensive desalting was required.

EXAMPLE 2

Preparation of Arginine/Lysine-Enriched Peptides from Pea Protein

A 15 w/w % pea protein (Propulse 975, ParrHeim Food, Canada) solution was prepared. 5% Alkalase was added and the pea protein was hydrolysed for 3 hrs at 60° C. Next, the pH was adjusted to 7.0 and the enzyme was inactivated by running the solution through a HTST (approx. 3 min at 110° C.). The solution was passed through a HFK131 ultrafiltration unit (Koch Membrane Systems, USA). The permeate was applied in the following process steps.

The permeate (hydrolysate solution) was diluted to contain 5% solids and was subsequently loaded onto cation exchange resin (Amberlite IRC 50, flow rate is 5 bed volumes/hr). The cation exchange resin was washed with 1 bed volume 50 mM phosphate buffer pH 7.0, followed by a second wash step with 2 bed volumes 0.5 M NaOH (flow rate during both wash steps is 5 bed volumes/hr). The arginine- and lysine-rich peptides were eluted with 3 bed volumes demineralised water.

The content of arginine, lysine and protein was determined as described in Example 1. The eluate contained the arginine- and lysine-enriched peptides with a purity level of 21 w/w % arginine and 21 w/w % lysine, based on total protein content.

The eluate fraction was adjusted to pH 7, and freeze-dried to obtain a powder product. The protein:salt (w/w) ratio was 11:2.

COMPARATIVE EXAMPLE 2A

Pea protein was hydrolysed as described in Example 2. The hydrolysate solution was loaded onto cation exchange resin Amberlite IRC 50 (flow rate=5 bed volumes/hr). Subsequently, the peptides were eluted with 1 M NaCl.

The content of arginine, lysine and protein was determined as described in Example 1. The obtained peptide fraction yielded arginine and lysine contents that were comparable to those achieved with the method of Example 2; However, the protein:salt ratio (w/w) was 1:9.5. The product had a 52 times higher salt content in comparison with the product of Example 2 and therefore required extensive desalting.

EXAMPLE 3

Formulation and Preparation of an Arginine/Lysine-Enriched Sports Drink

| Ingredients | |
|---|---|
| Recipe | Content (%) |
| Water | 90.4 |
| Maltodextrin (20 DE) | 4.0 |
| Fructose | 2.4 |
| Peptide preparation according to the invention | 3.0 |
| Flavour[1] | 0.2 |

[1]Flavouring agents can e.g. be lemon (93%; nr. 15913482, IFF, The Netherlands) or sweet lime (7%; nr. 75980279, IFF, The Netherlands).

The peptide preparation according to the invention is dissolved in the water, all the other ingredients are added to form a mixture and the pH of the mixture is adjusted with citric acid to pH 3.8. The mixture is filled into a holder, such as bottles or cans, and subsequently pasteurised.

The invention claimed is:

1. A process for the preparation of a mixture of peptides by cationic exchange chromatography, having an arginine and lysine content of at least 20 w/w %, based on the total amount of protein, from at least one protein source, comprising the steps of:
    a) cleaving the proteins of at least one protein source into peptides;
    b) allowing the peptides to bind to cation exchange resin;
    c) washing the cation exchange resin with an alkaline wash solution having a hydroxide normality of 0.05-2.0; and
    d) eluting bound peptides from the resin with an aqueous elution solution having an ionic strength of at most 200 mM and a pH between 5.0-9.0.

2. The process of claim 1, comprising between steps b) and c) a prewash step, wherein said cation exchange resin is washed with a prewash solution having an ionic strength of at most 200 mM and a pH between 5.0-9.0.

3. The process of claim 1, wherein the mixture of peptides has an arginine and lysine content of at least 30 w/w %, based on total amount of protein.

4. The process of claim 1, wherein step a) comprises enzymatic hydrolysis.

5. The process of claim 1, wherein step b) is preceded by a filtration step.

6. The process according to claim 5, wherein the filtration step is carried out with a membrane having a molecular weight cut-off of 10 kDa.

7. The process of claim 1, wherein the at least one protein source comprises at least two different proteins.

8. The process of claim 1, wherein the at least one protein source is of vegetable origin.

9. The process of claim 1, wherein the at least one protein source is chosen from the group, consisting of soy, pea and cotton seed.

10. The process of claim 1, wherein the at least one protein source comprises at least 21 w/w % arginine and lysine.

* * * * *